United States Patent
Turos et al.

(10) Patent No.: US 10,010,545 B1
(45) Date of Patent: *Jul. 3, 2018

(54) ANTIBIOTIC COMPOSITIONS AND METHODS OF USE

(71) Applicant: University of South Florida, Tampa, FL (US)

(72) Inventors: Edward Turos, Wesley Chapel, FL (US); Biplob Bhattacharya, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/497,365

(22) Filed: Apr. 26, 2017

Related U.S. Application Data (63) Continuation of application No. 14/208,330, filed on Mar. 13, 2014, now Pat. No. 9,670,179.

(60) Provisional application No. 61/781,106, filed on Mar. 14, 2013.

(51) Int. Cl.
*A61K 31/496* (2006.01)

(52) U.S. Cl.
CPC .................................. *A61K 31/496* (2013.01)

(58) Field of Classification Search
CPC .................................................... A61K 31/496
See application file for complete search history.

(56) References Cited

FOREIGN PATENT DOCUMENTS

EP  0366641 A2 * 5/1990 ........... C07D 401/12

OTHER PUBLICATIONS

"Estimates of Funding for Various Research, Condition, and Disease Categories (RCDC)", National Institutes of Health; Research Portfolio Online Reporting Tools (RePORT), https://report.nih.gov/PFSummaryTable.aspx, Table Published: Feb. 10, 2016, 9 pages.
National Action Plan for Combating Antibiotic-Resistant Bacteria, The White House Washington, Mar. 2015, pp. 1-63.
"Bad Bugs, No Drugs: No ESKAPE! An Update from the Infectious Diseases Society of America", Boucher et al., IDSA Report on Development Pipeline, CID 2009:48, Jan. 1, pp. 1-12.
113th Congress 1st Session, H.R. 2285, Authenticated US Government Information GPO, HR 2285 IH, Jun. 6, 2013, pp. 1-32.

\* cited by examiner

*Primary Examiner* — Kortney L. Klinkel
*Assistant Examiner* — Ibrahim D Bori
(74) *Attorney, Agent, or Firm* — Thomas | Horstemeyer, LLP (57) ABSTRACT

Embodiments of the present disclosure provide for compositions including an antibiotic containing a N-thiolated beta-lactam moiety, pharmaceutical compositions including the antibiotic, methods of treatment of a condition (e.g., bacterial infection), methods of treatment using compositions or pharmaceutical compositions, and the like.

4 Claims, 2 Drawing Sheets

Structure A

AA = Antimicrobial agent

Structure B

R=CH₃, sBu
R'=2-ClPh
R''=CH₃, pentyl, hexyl

ANTIBIOTIC COMPOSITIONS AND METHODS OF USE

CLAIM OF PRIORITY TO RELATED APPLICATION

This application is a continuation of U.S. utility application entitled "ANTIBIOTIC COMPOSITIONS AND METHODS OF USE", having Ser. No. 14/208,330 and filed on Mar. 13, 2014 (now U.S. Pat. No. 9,670,179, having issued on Jun. 6, 2017). U.S. utility application Ser. No. 14/208,330 claims priority to U.S. provisional application entitled "ANTIBIOTIC COMPOSITIONS AND METHODS OF USE" having Ser. No. 61/781,106, filed on Mar. 14, 2013, the contents of all of which are entirely incorporated herein by reference.

BACKGROUND

In spite of the rapid and continued emergence of drug resistant pathogens, there has been an alarming decline in drug discovery efforts in the pharmaceutical industry, leading to a 75% decline in FDA approval of antibacterial agents from 1983-2007. As a result, the IDSA issued a call to action, indicating that urgent necessity of developing sustainable antibacterial research and development that responds to current resistance trends, and anticipate the development of resistance in the future.

SUMMARY

Embodiments of the present disclosure provide for compositions including an antibiotic containing a N-thiolated beta-lactam moiety, pharmaceutical compositions including the antibiotic, methods of treatment of a condition (e.g., bacterial infection), methods of treatment using compositions or pharmaceutical compositions, and the like.

An embodiment of the present disclosure provides for a composition that includes: an antibiotic containing a N-thiolated beta-lactam moiety as shown by structure A:

Structure A

AA = Antimicrobial agent and, where AA is an antimicrobial agent, where R' is a substituted or unsubstituted aryl moiety, and where R is a substituted or unsubstituted, linear or branched, aliphatic moiety or a substituted or unsubstituted aryl moiety. In an embodiment, the antibiotic containing a N-thiolated beta-lactam moiety include the following structure:

where R" is selected from the group consisting of: a substituted or unsubstituted, linear or branched, aliphatic moiety.

An embodiment of the present disclosure provides for a pharmaceutical composition that includes: a therapeutically effective amount of an antibiotic containing the N-thiolated beta-lactam moiety having structure A, or a pharmaceutically acceptable salt of the antibiotic containing the N-thiolated beta-lactam moiety having structure A, and a pharmaceutically acceptable carrier, to treat a bacterial infection, where structure A is shown below:

Structure A

AA = Antimicrobial agent wherein AA is an antimicrobial agent, wherein R' is a substituted or unsubstituted aryl moiety, and wherein R is a substituted or unsubstituted, linear or branched, aliphatic moiety or a substituted or unsubstituted aryl moiety.

An embodiment of the present disclosure provides for a method of treating a bacterial infection that includes: delivering to a subject in need thereof, a pharmaceutical composition, wherein the pharmaceutical composition includes a therapeutically effective amount of an antibiotic containing the N-thiolated beta-lactam moiety as shown in structure A, or a pharmaceutically acceptable salt of the antibiotic containing N-thiolated beta-lactam moiety as shown in structure A, and a pharmaceutically acceptable carrier, to treat the condition, where structure A is shown below:

Structure A

AA = Antimicrobial agent where AA is an antimicrobial agent, wherein R' is a substituted or unsubstituted aryl moiety, and where R is a substituted or unsubstituted, linear or branched, aliphatic moiety or a substituted or unsubstituted aryl moiety.

Other compositions, methods, features, and advantages will be, or become, apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Before the present disclosure is described in greater detail, it is to be understood that this disclosure is not limited to particular embodiments described, and the embodiment of the disclosure as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of pharmacy, synthetic organic chemistry, chemistry, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like. The phrases "consisting essentially of" or "consists essentially" or the like, when applied to methods and compositions encompassed by the present disclosure refers to compositions like those disclosed herein, but which may contain additional composition components (or method steps). Such additional composition components (or method steps, etc.), however, do not materially affect the basic and novel characteristic(s) of the compositions (or methods), compared to those of the corresponding compositions or methods disclosed herein. "Consisting essentially of" or "consists essentially" or the like, when applied to compositions encompassed by the present disclosure have the meaning ascribed in U.S. Patent law and the term is open-ended, allowing for the presence of more than that which is recited (e.g., trace contaminants, non-active components (e.g., binders, etc), and the like) so long as basic or novel characteristics of that which is recited is not changed by the presence of more than that which is recited, but excludes prior art embodiments.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference.

Definitions

The term "substituted" refers to any one or more hydrogens on the designated atom that can be replaced with a selection from the indicated group, provided that the designated atom's normal valence is not exceeded, and that the substitution results in a stable compound. In an embodiment, one or more of the hydrogens can be substituted with a halogen, an alkyl group (unsubstituted or substituted), a cycloalkyl group (unsubstituted or substituted), an aryl group (unsubstituted or substituted), and the like. In particular, the term "substituted," as in "substituted alkyl", "substituted cycloalkyl," substituted aryl," and the like, means that the substituted group may contain in place of one or more hydrogens a group such as a halogen, an alkyl group (unsubstituted or substituted), a cycloalkyl group (unsubstituted or substituted), an aryl group (unsubstituted or substituted), and the like.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

As used herein, a "pharmaceutical composition" refers to a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use.

The term "pharmaceutically acceptable salts" refers to a compound of the present disclosure that can be modified by making acid or base salts thereof. Pharmaceutically acceptable salt refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Examples of pharmaceutically acceptable salts include, but are not limited to, mineral or organic acid salts of basic residues such as amines; and alkali or organic salts of acidic residues such as carboxylic acids.

In the event that embodiments of the present disclosure form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hem isulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

The term "unit dosage form," as used herein, refers to physically discrete units suitable as unitary dosages for human and/or animal subjects, each unit containing a predetermined quantity of a compound calculated in an amount sufficient (e.g., weight of host, disease, severity of the disease, etc) to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

The terms "effective amount" or "effective dose" as used herein refers to that amount of an embodiment of the present disclosure being administered to treat the bacterial infection.

As used herein, "treat", "treatment", "treating", and the like refer to acting upon a bacterial infection. The improvement or alteration may include an improvement in symptoms or an alteration in the physiologic pathways associated with the bacterial infection. "Treatment," as used herein, covers one or more treatments of a bacterial infection or disease in a subject (e.g., a mammal, typically a human or non-human animal of veterinary interest), and includes: treating a bacterial infection.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a bacterial infection.

The term "therapeutically effective amount" as used herein refers to that amount of an embodiment of the composition or pharmaceutical formulation being administered that will relieve to some extent one or more of the symptoms of infection being treated, and/or that amount that will prevent, to some extent, one or more of the symptoms of the infection that the subject being treated has or is at risk of developing.

By "administration" is meant introducing an embodiment of the present disclosure into a subject. Administration can include routes, such as, but not limited to, intravenous, oral, topical, subcutaneous, intraperitoneal, intraarterial, inhalation, vaginal, rectal, nasal, introduction into the cerebrospinal fluid, or instillation into body compartments can be used. A preferred route is oral administration.

As used herein, the term "subject" includes humans, mammals (e.g., cats, dogs, horses, etc.), and other living animals. In particular, the host is a human subject. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The phrase "bacterial infection" can refer to a bacteria colonizing a tissue or organ of a subject, where the colonization causes harm to the subject. The harm can be caused directly by the bacteria and/or by toxins produced by the bacteria. Reference to bacterial infection includes also includes bacterial disease. Antibiotic agents, such as those described herein, can kill bacteria, prevent bacterial growth, and/or assist the subjects ability to kill or prevent bacteria growth.

Bacteria that cause bacterial infection are called pathogenic bacteria. The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis,*

*Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, Peptococcus species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuro pneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae).

Discussion

Embodiments of the present disclosure provide for compositions including an antibiotic containing a N-thiolated beta-lactam moiety, pharmaceutical compositions including the antibiotic, methods of treatment of a condition (e.g., bacterial infection), methods of treatment using compositions or pharmaceutical compositions, and the like. In an embodiment, the antibiotic containing the N-thiolated beta-lactam moiety can be a prodrug. In an embodiment, the antibiotic containing the N-thiolated beta-lactam moiety is attached to one or more additional antibacterial agents (e.g., via enzymatic- or chemically-cleavable covalent linkages). Embodiments of the present disclosure can be bactericidal and/or bacteriostatic. Embodiments of the present disclosure can kill bacteria and/or stop the growth of bacteria.

An embodiment of the present disclosure includes a composition and pharmaceutical composition including an antibiotic containing the N-thiolated beta-lactam moiety. In an embodiment, the pharmaceutical composition and the method of treatment (e.g., of an infection such as one directly or indirectly caused by a bacterial infection) includes a therapeutically effective amount of the antibiotic containing the N-thiolated beta-lactam moiety, or a pharmaceutically acceptable salt of the antibiotic containing the N-thiolated beta-lactam moiety, and a pharmaceutically acceptable carrier, to treat a condition (e.g., bacterial infection).

In an embodiment the bacterial infections can be caused by one or more types of bacteria, in particular, drug or multidrug resistant bacteria. In an embodiment, the bacteria can include, but is not limited to, *Staphylococcus aureus, Streptococcus pyogenes, Streptococcus pneumonia, Enterococcus faecalis, Enterococcus faecium, Pseudomonas aeruginosa, Clostridium difficile, Escherichia coli, Salmonella, Acinetobacter baumannii, Mycobacterium tuberculosis,* or a combination thereof.

Figure 1:
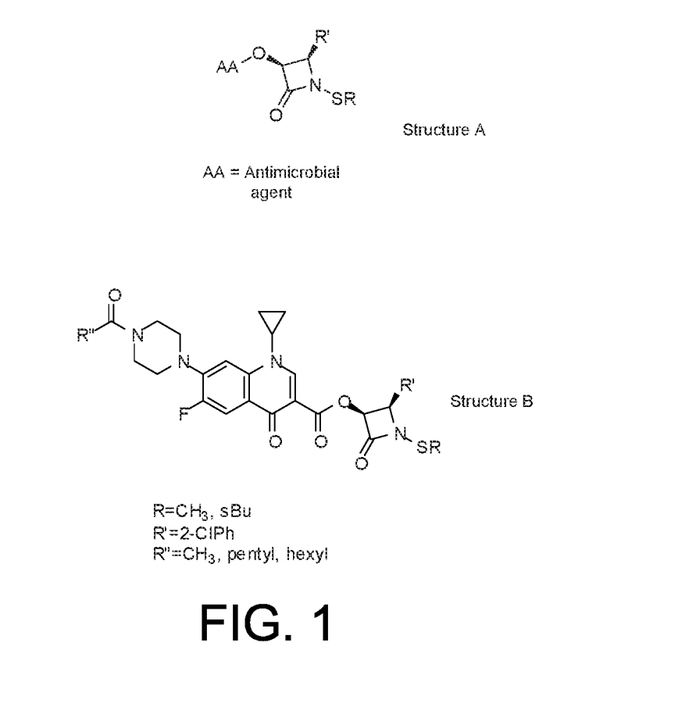
FIG. 1 illustrates embodiments of the antibiotic containing a N-thiolated beta-lactam moiety.
Figure 2:
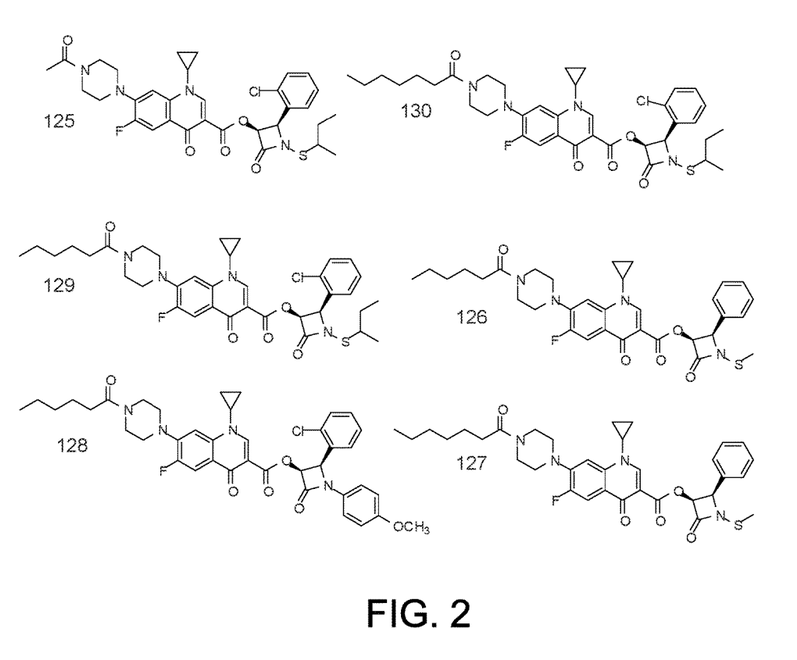
FIG. 2 illustrates embodiments of the antibiotic containing a N-thiolated beta-lactam moiety.

In an embodiment, the antibiotic containing the N-thiolated beta-lactam moiety can include a structure as shown in FIGS. 1 and 2, specifically the compounds as described by Structure A and Structure B. In an embodiment, R' can be a substituted or unsubstituted aryl moiety. In an embodiment, R can be a substituted or unsubstituted, linear or branched, aliphatic moiety such as a substituted or unsubstituted, linear or branched, alkyl moiety or R can be a substituted or unsubstituted aryl moiety. In an embodiment, R" can be a substituted or unsubstituted, linear or branched, aliphatic moiety such as a substituted or unsubstituted, linear or branched, alkyl moiety.

In an embodiment, AA is an antibiotic compound bonded to the N-thiolated beta-lactam moiety through the O on the N-thiolated beta-lactam as shown in FIGS. 1 and 2. In an embodiment, AA is bonded to the 0 on the N-thiolated beta-lactam in a manner that does not change or does not substantially change (e.g., the change can be about 10% or less, about 5% or less, about 2% or less, or about 1% or less) the bactericidal and/or bacteriostatic characteristics of AA. In an embodiment, AA can be slightly modified to bond to the N-thiolated beta-lactam moiety but still maintain or substantially maintain (e.g., maintains about 90% or more, about 95% or more, about 98% or more, or about 99% or more) its antibacterial characteristics. In an embodiment, the AA can bond via a hydrolytically-sensitive ester linkage (e.g., Scheme 1 in the Example).

In an embodiment, the AA can be bactericidal and/or bacteriostatic. In an embodiment, AA can include antibiotics in the fluoroquinolone class of antibiotics. In an embodiment, these include ciprofloxacin (Cipro), levofloxacin (Levaquin), ofloxacin (Floxin), gatifloxacin (Tequin), norfloxacin (Noroxin), moxifloxacin (Avelox), trovafloxacin (Trovan). In an embodiment, other AA can include penicillin and penicillin derivatives, cephalosporin and cephalosporin derivatives, monobactam and monobactam derivatives, carbapenem and carbapenem derivatives, and a combination thereof. In an embodiment, other AA can include polymixins and polymixins derivatives, rifamixycins and rifamixycin derivatives, lipiamycins and lipiamycins derivatives, sulfonamides and sulfonamide derivatives, and the like. In an embodiment, other AA can include cyclic lipopeptides and lipopeptide derivatives, glycylcyclines and glycylcyclines derivatives, oxazolidinones and oxazolidinones derivatives, and lipiarmycins and lipiarmycin derivatives.

As mentioned above, embodiments of the present disclosure include a method of treating a bacterial infection. The method can include delivering to a subject in need thereof, a pharmaceutical composition that includes a therapeutically effective amount of an antibiotic containing the N-thiolated beta-lactam moiety such as those shown in FIG. 1 or FIG. 2, or a pharmaceutically acceptable salt of the antibiotic containing N-thiolated beta-lactam moiety as shown in FIG. 1 or FIG. 2, and a pharmaceutically acceptable carrier, to treat the condition. In an embodiment, the antibiotic containing the N-thiolated beta-lactam moiety can be given to the subject periodically (e.g., hourly, daily, weekly, depending upon the infection) as needed to treat the infection. In addition, the antibiotic containing the N-thiolated beta-lactam moiety can be given to a subject prophylactically, where the subject may have a risk of infection. In an embodiment the bacterial infections can be caused by for more types of bacteria. In an embodiment, the types of bacteria can include: *Staphylococcus aureus, Streptococcus pyogenes, Streptococcus pneumonia, Enterococcus faecalis, Enterococcus faecium, Pseudomonas aeruginosa, Clostridium difficile, Escherichia coli, Salmonella, Acinetobacter baumannii, Mycobacterium tuberculosis*, or a combination thereof.

It should be noted that the therapeutically effective amount to result in uptake of the antibiotic containing the N-thiolated beta-lactam moiety into the host can depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.
Pharmaceutical Formulations and Routes of Administration Embodiments of the present disclosure include an antibiotic containing the N-thiolated beta-lactam moiety as identified herein and can be formulated with one or more pharmaceutically acceptable excipients, diluents, carriers and/or adjuvants. In addition, embodiments of the present disclosure include antibiotic containing the N-thiolated beta-lactam moiety formulated with one or more pharmaceutically acceptable auxiliary substances. In particular beta-lactamase inhibitor can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the antibiotic containing the N-thiolated beta-lactam moiety can be administered to the host using any means capable of resulting in the desired effect. Thus, the antibiotic containing the N-thiolated beta-lactam moiety can be incorporated into a variety of formulations for therapeutic administration. For example, the antibiotic containing the N-thiolated beta-lactam moiety can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the antibiotic containing the N-thiolated beta-lactam moiety may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the antibiotic containing the N-thiolated beta-lactam moiety can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the antibiotic containing the N-thiolated beta-lactam moiety can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the antibiotic containing the N-thiolated beta-lactam moiety can be utilized in aerosol formulation to be administered via inhalation. Embodiments of the antibiotic containing the N-thiolated beta-lactam moiety can be formulated into pressurized acceptable propellants such as dichlorodifluoromethane, propane, nitrogen and the like.

Furthermore, embodiments of the antibiotic containing the N-thiolated beta-lactam moiety can be made into suppositories by mixing with a variety of bases such as emulsifying bases or water-soluble bases. Embodiments of the beta-lactamase inhibitor can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the beta-lactamase inhibitor in a composition as a solution in sterile water, normal saline or another pharmaceutically acceptable carrier.

Embodiments of the antibiotic containing the N-thiolated beta-lactam moiety can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the beta-lactamase inhibitor can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the antibiotic containing the N-thiolated beta-lactam moiety can be accomplished using any of a variety of refillable, pump systems. Pumps provide consistent, controlled release over time. In some embodiments, the antibiotic containing the N-thiolated beta-lactam moiety can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the antibiotic containing the N-thiolated beta-lactam moiety) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the antibiotic containing the N-thiolated beta-lactam moiety are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the antibiotic containing the N-thiolated beta-lactam moiety adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the antibiotic containing the N-thiolated beta-lactam moiety may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the antibiotic containing the N-thiolated beta-lactam moiety described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the antibiotic containing the N-thiolated beta-lactam moiety can be administered to a host in one or more doses. Those of skill will readily appreciate that dose levels can vary as a function of the specific the antibiotic containing the N-thiolated beta-lactam moiety administered, the severity of the symptoms and the susceptibility of the subject to side effects. Preferred dosages for a given compound are readily determinable by those of skill in the art by a variety of means.

In an embodiment, multiple doses of the antibiotic containing the N-thiolated antibiotic containing the N-thiolated beta-lactam moiety are administered. The frequency of administration of the antibiotic containing the N-thiolated beta-lactam moiety can vary depending on any of a variety of factors, e.g., severity of the symptoms, and the like. For example, in an embodiment, the antibiotic containing the N-thiolated beta-lactam moiety can be administered once per month, twice per month, three times per month, every other week (qow), once per week (qw), twice per week (biw), three times per week (tiw), four times per week, five times per week, six times per week, every other day (god), daily (qd), twice a day (qid), or three times a day (tid). As discussed above, in an embodiment, the antibiotic containing N-thiolated beta-lactam moiety is administered continuously.

The duration of administration of the antibiotic containing the N-thiolated beta-lactam moiety analogue, e.g., the period of time over which the antibiotic containing the N-thiolated beta-lactam moiety is administered, can vary, depending on any of a variety of factors, e.g., patient response, etc. For example, the antibiotic containing the N-thiolated beta-lactam moiety in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the antibiotic containing the N-thiolated beta-lactam moiety) to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the antibiotic containing the N-thiolated beta-lactam moiety) can be administered in a single dose or in multiple doses.

Embodiments of the beta-lactamase inhibitor can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the beta-lactamase inhibitor. Where systemic delivery is desired, administration typically involves invasive or systemically absorbed topical or mucosal administration of pharmaceutical preparations.

In an embodiment, the antibiotic containing the N-thiolated beta-lactam moiety can also be delivered to the subject by enteral administration. Enteral routes of administration include, but are not limited to, oral and rectal (e.g., using a suppository) delivery.

Methods of administration of the antibiotic containing the N-thiolated beta-lactam moiety through the skin or mucosa include, but are not limited to, topical application of a suitable pharmaceutical preparation, transdermal transmission, injection and epidermal administration. For transder- mal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

Example

Synthesis of N-Acyl Ciprofloxacin-β-Lactam Dual-Action Drugs:

Coupling of the lactam with the N-acyl ciprofloxacin using EDCl/DMAP in dichloromethane yielded the desired coupled product. (Scheme 1)

Reaction conditions were optimized to get the best results, owing to the limited reactivity of the C-3 carboxylic acid of the ciprofloxacin and C-3 secondary alcohol of N-thiolated β-lactam. Other coupling reagents were tried but without much success. Finally, the EDCl/DMAP coupling worked best when the N-thiolated β-lactam (dissolved in dichloromethane) was added to a stirred mixture of the N-acyl ciprofloxacin in dichloromethane under chilled reaction conditions. The reaction mixture was slowly brought to room temperature with continuous stirring. Completion of the reaction was checked using TLC, and then the solution was concentrated under vacuum. The reactions may take 24 or more hours to yield an appropriate amount of the desired products. Six N-acyl ciprofloxacin-N-thiolated β-lactam derivatives were synthesized as per this scheme.

To explore the carboxylic acid side chain of the N-acyl ciprofloxacin, coupling with C3-hydroxylated N-thiolated β-lactams the ester linkages were used rather than the already exhausted use of the amine side chain. Esters are easily cleavable inside the cell, so that the carboxylic side chain of the N-acyl ciprofloxacin could then be free to bind to the DNA gyrase complex.

The activity of N-thiolated β-lactams comes from the presence of the organothio moiety in the structure, thus, several analogs were made using N-methylthio β-lactam and N-sec-butylthio β-lactam. One compound was synthesized with a p-methoxyphenyl group as a control because we presume it would not show any synergistic activity from the N-thiolated β-lactam portion but only from the hydrolytically-released ciprofloxacin Purification and Characterization of N-Acyl Ciprofloxacin-β-Lactam Dual-Action Prodrugs.

Column chromatography was first used to purify the acylation products, but it was found that this alone did not give the pure compounds. Waters Prep-LC instrument with Agilent Eclipse XDB-C18 column was then used to extract the pure compound from the crude mixture. Inside Agilent Eclipse XDB-C18, an ultra-high pure silicon dioxide ($SiO_2$), Zorbax Rx-SIL porous silica support was chemically bonded to a dense monolayer of dimethyl-n-octadecylsilane stationary phase. Water and acetonitrile (MeCN) with 0.05% TFA was used as a solvent system for mobile phase. Product purification was confirmed using LC-MS and NMR spectroscopy. High Resolution NMR was used to collect 1H NMR, 19F NMR and COSY data. $^1$H NMR has been labeled for structural characterization. $^{19}$F NMR shows a single peak because of the fluorine (F) group attached on ciprofloxacin. LCMS shows the mol. wt base peak of 640.19 confirming the compound.

Similar data was collected for analogs (FIG. 2). Each gave corresponding proof of structure in particular, the crucial presence of equimolar amount of the N-acyl ciprofloxacin and N-thiolated β-lactam, and the requisite O-acylated linkage to the β-lactam. After all the purification steps, there was unfortunately barely a small amount of purified compound 130 left to do a 1H NMR. Thus, a cold probe 500 MHz NMR spectrometer was used to collect the spectral information. The compound still contained a small amount of impurities but shows characteristic NMR signals of the acylation.

Attempted Synthesis of Penicillin G-N-Thiolated β-Lactams Dual-Action Drugs:

Biological Testing:

Six analogs (FIG. 2) of the ciprofloxacin-N thiolated β-lactam were successfully synthesized. All these compounds were then tested against ESKAPE pathogens for bioactivity. The ESKAPE pathogens are a collection of six deadly superbugs, *Enterococcus faecium, Staphylococcus aureus, Klebsiella pneumoniae, Acinetobacter baumannii, Pseudomonas aeruginosa*, and *Enterobacter* species. Each compound was tested in triplicates and it was observed that the compounds do not show any activity when tested for growth at all concentrations against *E. faecium, K. pneumoniae, A. baumannii, P. aeruginosa*, and *E. cloacae*. Compounds 125 and 130 displayed very good bioactivity against *S. aureus*, with MIC values of 1 μg/ml and 10 μg/ml, respectively. Each table below depicts whether growth was observed for each of the bacterial species. G denotes growth and X denotes no growth in the tables.

| G | Growth |
|---|--------|
| X | No Growth |

TABLE 4.1

Activity against *Enterococcus faecium*.

| lactam | 1 µg/ml | 2 µg/ml | 3 µg/ml | 4 µg/ml | 5 µg/ml | 6 µg/ml | 7 µg/ml | 8 µg/ml | 9 µg/ml | 10 µg/ml | 25 µg/ml |
|---|---|---|---|---|---|---|---|---|---|---|---|
| 125 | G | G | G | G | G | G | G | G | G | G | G |
| 126 | G | G | G | G | G | G | G | G | G | G | G |
| 127 | G | G | G | G | G | G | G | G | G | G | G |
| 128 | G | G | G | G | G | G | G | G | G | G | G |
| 129 | G | G | G | G | G | G | G | G | G | G | G |
| 130 | G | G | G | G | G | G | G | G | G | G | G |

TABLE 4.2

Activity against *Staphylococcus aureus*.

| lactam | 1 µg/ml | 2 µg/ml | 3 µg/ml | 4 µg/ml | 5 µg/ml | 6 µg/ml | 7 µg/ml | 8 µg/ml | 9 µg/ml | 10 µg/ml | 25 µg/ml |
|---|---|---|---|---|---|---|---|---|---|---|---|
| 125 | X | X | X | X | X | X | X | X | X | X | X |
| 126 | G | G | G | G | G | G | G | G | G | G | G |
| 127 | G | G | G | G | G | G | G | G | G | G | G |
| 128 | G | G | G | G | G | G | G | G | G | G | G |
| 129 | G | G | G | G | G | G | G | G | G | G | G |
| 130 | G | G | G | G | G | G | G | G | G | X | X |

TABLE 4.3

Activity against *Klebesiella pneumonia*.

| lactam | 1 µg/ml | 2 µg/ml | 3 µg/ml | 4 µg/ml | 5 µg/ml | 6 µg/ml | 7 µg/ml | 8 µg/ml | 9 µg/ml | 10 µg/ml | 25 µg/ml |
|---|---|---|---|---|---|---|---|---|---|---|---|
| 125 | G | G | G | G | G | G | G | G | G | G | G |
| 126 | G | G | G | G | G | G | G | G | G | G | G |
| 127 | G | G | G | G | G | G | G | G | G | G | G |
| 128 | G | G | G | G | G | G | G | G | G | G | G |
| 129 | G | G | G | G | G | G | G | G | G | G | G |
| 130 | G | G | G | G | G | G | G | G | G | G | G |

TABLE 4.4

Activity against *Acinetobacter baumannii*.

| lactam | 1 µg/ml | 2 µg/ml | 3 µg/ml | 4 µg/ml | 5 µg/ml | 6 µg/ml | 7 µg/ml | 8 µg/ml | 9 µg/ml | 10 µg/ml | 25 µg/ml |
|---|---|---|---|---|---|---|---|---|---|---|---|
| 125 | G | G | G | G | G | G | G | G | G | G | G |
| 126 | G | G | G | G | G | G | G | G | G | G | G |
| 127 | G | G | G | G | G | G | G | G | G | G | G |
| 128 | G | G | G | G | G | G | G | G | G | G | G |
| 129 | G | G | G | G | G | G | G | G | G | G | G |
| 130 | G | G | G | G | G | G | G | G | G | G | G |

TABLE 4.5

| | Activity against *Pseudomonas aeruginosa*. | | | | | | | | | | |
|---|---|---|---|---|---|---|---|---|---|---|---|
| lactam | 1 µg/ml | 2 µg/ml | 3 µg/ml | 4 µg/ml | 5 µg/ml | 6 µg/ml | 7 µg/ml | 8 µg/ml | 9 µg/ml | 10 µg/ml | 25 µg/ml |
| 125 | G | G | G | G | G | G | G | G | G | G | G |
| 126 | G | G | G | G | G | G | G | G | G | G | G |
| 127 | G | G | G | G | G | G | G | G | G | G | G |
| 128 | G | G | G | G | G | G | G | G | G | G | G |
| 129 | G | G | G | G | G | G | G | G | G | G | G |
| 130 | G | G | G | G | G | G | G | G | G | G | G |

CONCLUSION

Synthesis of dual drugs for the antibacterial purposes is a huge arena of research and for the first time this was done with the N-thiolated β-lactams. Though both N-acyl ciprofloxacins and N-thiolated β-lactams have been independently studied, the attempt to combine them via a cleavable covalent bond was never done. This study has elaborated on the synthesis of six such analogs. Lactam 125 shows complete growth inhibition at 1 µg/ml against MRSA.

Bacterial resistance is continuously increasing and it is a huge concern as the number of new drugs that has been cleared by FDA in the last 20 years has fallen drastically. Since a single drug is not always sufficient to control diseases or stop resistance on its own, it is an excellent idea to use a combination of drugs with different pharmacotherapeutic profiles.

Coupling of aztreonam-N-thiolated β-lactams, penicillin-N-thiolated β-lactams, Moxifloxacin-N-thiolated β-lactams etc. can satisfy some of this need, particularly in regards to the resistance in drug-resistant mutant strains.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A method of treating a bacterial infection comprising: delivering to a subject in need thereof, a pharmaceutical composition, wherein the pharmaceutical composition includes a therapeutically effective amount of an antibiotic containing a N-thiolated beta-lactam moiety as shown by structure A:

AA = Antimicrobial agent wherein R' is a $C_6$-$C_{14}$ substituted or unsubstituted aryl moiety, wherein R is a $C_1$-$C_{20}$ substituted or unsubstituted, linear or branched, aliphatic moiety or a $C_6$-$C_{14}$ substituted or unsubstituted aryl moiety, wherein AA is an antibiotic compound bonded to the 0 on the N-thiolated beta-lactam moiety, and wherein AA is a is an antibiotic compound from the fluoroquinolone class of antibiotics.

2. The method of claim 1, wherein the antibiotic containing a N-thiolated beta-lactam moiety has the following structure:

wherein R" is selected from the group consisting of: a $C_1$-$C_{20}$ substituted or unsubstituted, linear or branched, aliphatic moiety.

3. The method of claim 1, wherein the antibiotic containing a N-thiolated beta-lactam moiety has one of the following structures:

or

4. The method of claim 1, wherein the bacterial infection is caused by *Staphylococcus aureus, Streptococcus pyogenes, Streptococcus pneumonia, Enterococcus faecalis, Enterococcus faecium, Pseudomonas aeruginosa, Clostridium difficile, Escherichia coli, Salmonella, Acinetobacter baumannii, Mycobacterium tuberculosis, Klebsiella pneumoniae*, other *Enterobacter* species, or a combination thereof.

* * * * *